United States Patent [19]

Nigam

[11] Patent Number: 4,948,540
[45] Date of Patent: Aug. 14, 1990

[54] METHOD OF PREPARING COLLAGEN DRESSING SHEET MATERIAL

[75] Inventor: Alok Nigam, Phoenixville, Pa.

[73] Assignee: Semex Medical, Inc., Malvern, Pa.

[21] Appl. No.: 229,069

[22] Filed: Aug. 1, 1988

[51] Int. Cl.$^5$ .................. C08L 89/00; B29B 13/04
[52] U.S. Cl. .................... 264/28; 264/101; 264/236; 264/320; 264/347; 128/156; 128/DIG. 8
[58] Field of Search ............... 264/28, 101, 236, 320, 264/347; 128/DIG. 8, 156

[56] References Cited

U.S. PATENT DOCUMENTS

| | | | |
|---|---|---|---|
| 2,823,212 | 7/1974 | Chvapil | 264/28 |
| 2,934,446 | 4/1960 | Highberger et al. | 128/DIG. 8 |
| 2,934,447 | 4/1960 | Highberger et al. | 128/DIG. 8 |
| 3,071,483 | 1/1963 | Tu | 128/DIG. 8 |
| 3,632,361 | 1/1972 | Battista | 106/122 |
| 4,279,812 | 7/1981 | Cioca | 260/123.7 |
| 4,295,894 | 10/1981 | Cioca et al. | 106/155 |
| 4,327,195 | 4/1982 | Cioca et al. | 521/102 |
| 4,374,121 | 2/1983 | Cioca | 424/19 |
| 4,389,487 | 6/1983 | Ries | 435/273 |
| 4,412,947 | 11/1983 | Cioca | 260/123.7 |
| 4,515,637 | 5/1985 | Cioca | 424/94 |
| 4,597,762 | 7/1986 | Walter et al. | 623/1 |
| 4,600,533 | 7/1986 | Chu | 530/356 |
| 4,655,980 | 4/1987 | Chu | 128/DIG. 8 |
| 4,703,108 | 10/1987 | Silver et al. | 128/DIG. 8 |
| 4,725,671 | 2/1988 | Chu et al. | 128/DIG. 8 |

FOREIGN PATENT DOCUMENTS 1347582 2/1972 United Kingdom.

OTHER PUBLICATIONS

Brienza, E. et al., "The Use of Collagen Film as a Dressing for Skin Wounds," in Riv. Ital. Chir. Plastica, vol. 16 (1984) pp. 721–727.

Khosla, A. S. et al., "Mechanical Response of Reconstituted, Freeze-Dried Collagen Under Compressive Loads," in J. Biomechanics, vol. 17, No. 7 (1984) pp. 491–499.

Primary Examiner—Hubert C. Lorin
Attorney, Agent, or Firm—Webb, Burden, Ziesenheim & Webb

[57] ABSTRACT

A mechanically stable, conformable collagen wound dressing sheet material is fabricated by lyophilizing (freeze-drying) a collagen composition and compressing the porous pad thus produced at a pressure between about 15,000–30,000 p.s.i. The sheet material thus produced may also be treated with optional dehydrothermal crosslinking known in the art. In addition to mechanical stability and conformability, the sheet material demonstrates high absorptivity, i.e., about 15–20 times its weight in isotonic saline, making it highly useful as a medical or surgical dressing or as a carrier for other medicaments such as antibiotics. The sheet material may be impregnated with thrombin.

8 Claims, No Drawings

METHOD OF PREPARING COLLAGEN DRESSING SHEET MATERIAL

FIELD OF THE INVENTION

The present invention relates to wound dressing sheet materials prepared from collagen.

INTRODUCTION

Collagen, and collagen-containing materials, have been widely used in the cosmetic, medical and surgical care of the skin. In fact, development of collagen healing solutions for surgical applications paralleled the widespread adoption of collagen materials in general skin care cosmetic products. In a more limited way, solid collagen articles have been adapted for medical and surgical use, and various wound dressing materials incorporate collagen in different ways and in different forms.

Generally, however, collagen sheet materials themselves have had limited application as wound dressing materials due to their excessive porosity and poor conformability. For example, wound dressing materials prepared from collagen solutions freeze-dried in sheet form are characterized by a flaky, nonpliable, low-density structure which does not adequately conform to the anatomy for satisfactory topical use.

BACKGROUND OF THE INVENTION

U.S. Pat. No. 4,412,947 to Cioca discloses a collagen sponge and a method for preparing it; as disclosed in Example II, the sponge may be in the form of a sheet and is suitable for use as a wound dressing, burn dressing, hemostatic sheet or the like. U.S. Pat. No. 3,632,361 to Battista discloses a water-insoluble, highly absorbent body or mat of collagen formed by freeze-drying, in a mold, a dispersion of collagen in aqueous medium. U.S. Pat. No. 4,600,533 to Chu, entitled "Collagen Membranes for Medical Use," discloses a gel of collagen which is compressed to a mat, then dried, or a gel which is centrifuged, then dried. No freeze-drying is used in the Chu process.

Additional prior art collagen products are disclosed in a number of additional references, including Khosla, A.S. et al., "Mechanical Response of Reconstituted, Freeze-Dried Collagen Under Compressive Loads," *J. Biomechanics*, Vol. 17, No. 7 (1984) pp. 491499, and a number of United States patents. These U.S. patents include U.S. Pat. No. 4,279,812, U.S. Pat. No. 4,295,894, U.S. Pat. No. 4,327,195, U.S. Pat. No. 4,374,121, U.S. Pat. No. 4,412,947, and U.S. Pat. No. 4,515,637 all to Cioca, British Patent No. 347,582 to Cioca, U.S. Pat. No. 4,597,762 to Walter et al. and U.S. Pat. No. 4,389,487 to Ries. The aggregate prior art as cited discloses collagen articles which may form pelts, may include polyurethanes and other materials, may be prepared either into wooly materials or prostheses, i.e., breast implants, etc., and generally may provide a specialized function for a given medical or surgical application.

Notwithstanding the variety of materials taught by the prior art, the references identified above do not teach or suggest the solution to the ubiquitous problem of high porosity and excessive resilience in collagen and collagen-containing sheet materials. Accordingly, a need remains for a wound dressing or hemostatic sheet material, prepared primarily of collagen, which has improved mechanical stability and is adequately dense and sufficiently conformable for topical medical/surgical utility.

SUMMARY OF THE INVENTION

In order to meet this need, the present invention is a mechanically stable, conformable collagen wound dressing sheet material fabricated by lyophilizing (freeze-drying) a specialized collagen suspension, in which the ratio of soluble to insoluble collagen is maintained in the range of 1:20 to 10:1, and compressing the porous pad thus produced at a pressure between about 15,000–30,000 p.s.i. to a thickness between 25 and 40 percent of its starting thickness. The sheet material thus produced may also be treated with optional dehydrothermal crosslinking known in the art. In addition to mechanical stability and conformability, the sheet material demonstrates high absorptivity, i.e., about 15–20 times its weight in isotonic saline, making it highly useful as a medical or surgical dressing or as a carrier for other medicaments such as antibiotics. The sheet material may be impregnated with thrombin.

DETAILED DESCRIPTION OF THE INVENTION

Prior to the lyophilization and compression which characterize the present invention, preparation of the starting collagen suspension is carried out as follows. Because the collagen suspension of the present invention contains both soluble and insoluble collagen, the soluble collagen and insoluble collagen fibers are first prepared separately, then combined.

"Natural insoluble collagen" as used herein means and refers to collagen which cannot be dissolved in an aqueous alkaline or in any inorganic salt solution without chemical modification, and includes hides, splits and other mammalian or reptilian coverings. More particularly, "natural insoluble collagen" refers to collagen derived from the corium, which is the intermediate layer of a bovine hide between the grain and the flesh sides. In young animals there is little intermolecular and/or interfibrillar crosslinking, which provides for some degree of solubility of the collagen. Soluble collagen is therefore most often derived from young animal skins. During the aging process, however, both intermolecular and interfibrillar crosslinking occurs, yielding primarily insoluble collagen immature hides.

Both the soluble collagen and the natural insoluble collagen fibers ("native collagen fibers") in accordance with the present invention are preferably derived from bovine hides. The soluble collagen is ordinarily, for the reason identified above, derived from calf hides. The hides are dehaired by liming, degreased to produce substantially pure native collagen fibers, and granulated to a particle size of less than 1 millimeter, and preferably less than 0.5 millimeters. The degreasing and granulation can be accomplished with materials, apparatus and methods known to those skilled in the art. In contrast with the soluble collagen, it is important that the final "native collagen fibers⇌ retain their crosslinkages, i.e., insolubility in water, aqueous acid, aqueous base or salt, but yet remain substantially pure so as to maintain the nonantigenic and nonallergenic characteristics recognized in native collagen generally.

Although both insoluble collagen fibers and soluble collagen may be prepared by means known in the art, for the purpose of the preparation of the present sheet material the methods outlined in the following Examples I and II are particularly preferred.

EXAMPLE I

Lime splits from young calf skins were washed with three times their weight of water with agitation for one hour. The agitation/washing step was repeated three times for a total of four repetitions of the washing step. The skins were then washed for four hours within three times the hide weight 3% ammonium chloride solution. At the end of four hours, because deliming was not complete (pH of ground-up calf skin in deionized water was not less than 7.5), the ammonium chloride solution was repeated. The delimed calf skins were then washed in three times the weight of the hides of water for one hour. This water wash was repeated two additional times, for a total of three water washes.

The delimed and washed calf skins were then treated for 48 hours with three times the hide weight of a solution comprised of 2.5 N. sodium hydroxide combined with 1 normal sodium sulfate. The calf skins were then washed for four hours with three times their weight of 1N. sodium sulfate. The hides were then drained and washed with water until free of washable sulfate ions, as tested by precipitation with barium chloride solution.

The calf skins thus treated were neutralized with acetic acid. (Citric, lactic and hydrochloric acids could have been substituted.) The hides were washed continuously with deionized water for 2 hours, with the total amount of water being used equal to four times the weight of the calf skins. Subsequently, in six times their weight of water, the calf skins were homogenized, the pH of the homogenate was adjusted to 4.5 with acetic acid, and the mixture was centrifuged to remove particulates. The particulates thus obtained were resuspended in deionized water adjusted to pH 4.5 and were centrifuged again. This process was repeated 2 more times, for a total of 4 acid treatment/centrifugation cycles.

The precipitated and centrifuged collagen fibrils were then lyophilized at a temperature of $-60°$ C. and vacuum of $10^{-3}$–$10^{-5}$ torr for 48 hours, with final temperature maintenance at 20° C. for at least 8 hours. Cooling was achieved at a rate of 25° C. per hour. Dried collagen obtained from this lyophilization step was ground and extracted with acetone—isopropanol, ethanol, heptane or pentane could have been substituted—to remove any residual fat and organic extractable impurities. The purified collagen so obtained was vacuum dried and redissolved in deionized water to make a 1% solution at a pH of 3.0–4.0. The pH of the soluble collagen thus produced was adjusted using acetic acid, although the citric and lactic acids suitable for use in the neutralization of the calf skin, discussed above, could have been substituted. The purified soluble collagen solution thus prepared was filtered through a 60 micron filter.

EXAMPLE II

In order to prepare insoluble native collagen fibers, lime bovine splits were cut into ¼ inch pieces and were washed with three times their weight of water for two hours with agitation. The bovine split pieces were drained and the water washing process was repeated. The hide pieces were then neutralized and adjusted to a pH between 5 and 5.5 with acetic acid; citric, propionic or benzoic acids would have been suitable. Total acid concentration was maintained between 0.5 and 1%, and acid solution equal to 3 times the weight of the hides was used. The hide pieces were allowed to remain in contact with the acid solution for 4½ hours, after which the hide pieces registered a pH of 5.8.

The neutralized collagen pieces were then ground with a continuous stream of water in a single rotary plate type disc mill, with plate separation 0.0 to 5 millimeters. The collagen fibers thus produced were dewatered by freezing and thawing. A resultant relatively concentrated fiber mass was then lyophilized, with cooling at a rate of 20°–25° C./hr to a final temperature of $-20°$ C. to $-60°$ C., with vacuum sublimation at 125 millitorr. Lyophilization was complete when the final temperature of $-20°$ C. to $-60°$ C. was maintained for at least 8 hours.

The lyophilized cake was reduced to fine fibers between 4 and 40 mesh using a microcutter mill. The fine fibrous collagen material thus obtained was extracted with ethanol; acetone, hexane and other organic solvents followed by vacuum drying for solvent evolution were likewise suitable.

In order to prepare the present collagen sheet material, soluble collagen and insoluble native collagen fibers are admixed in aqueous solution. The ratio of soluble to insoluble collagen is maintained in the range of 1:20 to 10:1. For example, soluble collagen prepared in accordance with Example I may be admixed with insoluble native collagen fibers, as prepared in Example II, by blending the two aqueous preparations so produced. Blending of a collagen solution with a collagen suspension in this manner may be accomplished by high speed blending in, for example, a Waring ® blender.

Ordinarily, insoluble native collagen fiber is incorporated in the range of 0.5 to 5% of the total mixture, with a preferable inclusion of insoluble collagen fiber in the amount of approximately 5% by weight of the total weight of the solution. The pH of the solution should be adjusted to within the range of 3–7, preferably 4.5–5.5, using organic acids or sodium hydroxide as needed.

The blended mixture containing both soluble and insoluble collagen is sterilized, by irradiation for example, and is poured into trays, such as stainless steel or polyethylene trays, to a depth of between 0.2 to 2 centimeters. The slurry is subsequently lyophilized. Cooling is ordinarily achieved at between 10°–20° C./hr, final temperature of $-20°$ C. to $-60°$ C., with sublimation in 100–150 millitorr vacuum at the final temperature of $-20°$ C. to $-60°$ C.

Sheet material prepared as described is then compressed to a thickness of between 0.1 to 0.5 centimeters at a pressure of between 15,000–30,000 p.s.i., to yield a collagen dressing sheet material having high absorptivity, i.e., 15–20 times its weight, which also has a good dry and weight and mechanical strength and good conformability to shape. Mechanical strength may be enhanced with the optional dehydrothermal crosslinking techniques (heat and vacuum) known in the art.

Optionally, the sheet material thus produced may be impregnated with thrombin. For example, the sterile sheet material may be immersed in or contacted with a sterile filtered aqueous solution of thrombin containing between 10,000–50,000 units per liter. After impregnation, a subsequent final lyophilization step yields a sheet material containing 20–100 i.u. thrombin per square inch.

Although the invention has been described with respect to the special materials and embodiments above, the invention is to be limited only insofar as is set forth in the accompanying claims.

I claim:

1. A method of preparing a collagen dressing sheet, including the steps of:
   (a) selecting an aqueous composition containing both soluble collagen and native collagen fibers;
   (b) charging the composition of step (a) to a mold;
   (c) lyophilizing said composition in said mold to yield a collagen mat having a thickness between 0.2–2 centimeters;
   (d) compressing said collagen mat at a pressure of between 15,000–30,000 p.s.i. to a thickness of between 0.1–0.5 centimeters;
   whereby the compressing of said mat imparts high absorptivity thereto.

2. The process according to claim 1 wherein step (a) further comprises the step of:
   (a) admixing, in aqueous medium, soluble collagen and native collagen fibers.

3. The process according to claim 2 wherein the mold of step (b) is selected to have base dimensions substantially greater than depth dimensions.

4. The process according to claim 3 wherein step (c) further comprises the step of:
   (c) lyophilizing said composition in said mold at a temperature of $-60°$ C. and vacuum of $10^{-3}$–$10^{-5}$ torr for 48 hours with final temperature maintenance at $20°$ C. for at least 8 hours.

5. The process according to claim 2 wherein step (a) further comprises the step of:
   (a) admixing, in aqueous medium, soluble collagen in the amount of 0.5–10% by weight and native collagen fibers in the amount of 0.5–5% by weight.

6. The process according to claim 2 wherein step (a) further comprises the step of:
   (a) admixing, in aqueous medium, soluble collagen in the amount of 5.0% by weight and native collagen fibers in the amount of 5.0% by weight.

7. The process according to claim 6 further comprising the step of:
   (e) contacting said collagen mat with thrombin.

8. The process according to claim 7 further comprising the step of:
   (d) compressing and dehydrothermally crosslinking said collagen mat at a pressure of between 15,000–30,000 p.s.i. to a thickness of between 0.1–0.5 centimeters.

* * * * *